United States Patent [19]

Shitaokoshi et al.

[11] Patent Number: 4,705,497

[45] Date of Patent: Nov. 10, 1987

[54] BLOOD RESERVOIR

[75] Inventors: Sachiro Shitaokoshi; Mamoru Sekiguchi; Toshiaki Takagi, all of Fujinomiya; Toshimichi Mori, Tokyo, all of Japan

[73] Assignee: Terumo Kabushiki Kaisha, Tokyo, Japan

[21] Appl. No.: 868,094

[22] Filed: May 28, 1986

[30] Foreign Application Priority Data

May 31, 1985 [JP] Japan .................. 60-116509

[51] Int. Cl.$^4$ .......................................... A61M 37/00
[52] U.S. Cl. ......................................... 604/4; 210/927
[58] Field of Search ....................... 604/4–10; 210/927

[56] References Cited

U.S. PATENT DOCUMENTS

| | | | |
|---|---|---|---|
| 3,701,433 | 10/1972 | Krakaner et al. | 210/927 |
| 3,993,067 | 11/1976 | Schachet et al. | |
| 4,033,345 | 7/1977 | Sorenson et al. | 604/4 |
| 4,047,526 | 9/1977 | Reynolds et al. | 604/4 |
| 4,157,965 | 6/1979 | Raible . | |
| 4,208,193 | 6/1980 | Munsch et al. | |
| 4,243,531 | 1/1981 | Crockett et al. | 210/927 |
| 4,443,220 | 4/1984 | Haner et al. | 604/4 |

FOREIGN PATENT DOCUMENTS 122748 10/1984 European Pat. Off. .
146708 7/1985 European Pat. Off. .

Primary Examiner—C. Fred Rosenbaum
Assistant Examiner—Gene B. Kartchner
Attorney, Agent, or Firm—Frishauf, Holtz, Goodman & Woodward

[57] ABSTRACT

A blood reservoir, commonly used in a blood circuit with an artificial lung, includes a blood extraction line chamber provided inside a housing and having a blood extraction line connection port, the chamber temporarily accommodating blood from a vena cava received via the connection port, a suction line chamber provided inside the housing and having a suction line connection port, the chamber temporarily accommodating blood, drawn in during open-heart surgery, received via the connection port, a blood pooling chamber provided inside the housing and communicating with the blood extraction line chamber and the suction line chamber for pooling blood accommodated by the two chambers, filtering/defoaming member arranged to communicate the suction line and blood pooling chambers for filtering and defoaming blood accommodated in the suction line chamber, an extracted blood inflow tube having one end communicating with the blood extraction line connection port and another end open to the blood extraction line chamber, and a blood dispersing plate provided at and open end of the inflow tube and opposing a bottom portion of the blood extraction line chamber across a predetermined distance.

16 Claims, 6 Drawing Figures

BLOOD RESERVOIR

BACKGROUND OF THE INVENTION

This invention relates to a blood reservoir for temporarily storing or pooling blood extracted from a living body, and more particularly, to a blood reservoir used in a blood circuit having an artificial lung employed during extracorporeal circulation of blood at the time of open-heart surgery.

FIG. 1 is a circuit diagram schematically illustrating a blood circuit having an artificial lung in accordance with the prior art. In the arrangement shown in FIG. 1, blood extracted from a patient's aorta is fed into a blood reservoir 2 through a blood extraction line 1. During open-heart surgery, blood resulting from hemorrhage and blood filling the left ventricle or right auricle of the heart are drawn in via a suction line 3 and pump 4 and recovered in a cardiotomy reservoir 5. Thereafter, the blood so recovered is introduced into the blood reservoir 2. The blood thus pooled in the blood reservoir 2 is fed into a heat exchanger-type artificial lung 7 by a pump 6. In the artificial lung 7, the blood is adjusted in temperature and oxygenated before being returned to the patient by a blood delivery line 8. In addition to defoaming and pooling functions for the blood drawn from the patient during open-heart surgery, the cardiotomy reservoir 5 also functions to filter out foreign matter such as tissue and microaggregates entrained in the blood drawn in from the patient or present in a transfusion.

However, the above-described conventional blood circuit having an artificial lung is disadvantageous in that since both the blood reservoir 2 and cardiotomy reservoir 5 are provided, a large amount of blood circulates extracorporeally during open-heart surgery. In addition, owing to the presence of both the blood reservoir 2 and cardiotomy reservoir 5, the blood circuit has a complicated arrangement and requires considerable time to be assembled. Furthermore, it is necessary that the levels at which blood is pooled in both the blood reservoir 2 and cardiotomy reservoir 5 be maintained at safe levels which will assure that bubbles will not be entrapped in the blood. However, monitoring the blood pooling levels in both of the reservoirs is a complicated task.

It is desired that the blood reservoir 2 allows blood to flow in from the blood extraction line 1 under conditions in which microbubbles will not be formed in the blood, and that the reservoir 2 be capable of discharging air, separated from the blood in the form of air bubbles, into an exterior space in a reliable manner.

SUMMARY OF THE INVENTION

The present invention is contrived in the light of above-mentioned circumstances, and a primary object of the present invention is intended to provide a blood reservoir which allows a reduction in the amount of extracorporeally circulating blood during open-heart surgery, which makes it easier to assemble the circuit with the artificial lung and to monitor the blood pooling level, and which enables entrant blood from the blood extraction line to flow in under conditions in which microbubbles are not produced in the blood.

Another object of the present invention is intended to provide a blood reservoir which enables the air in bubbles separated from blood flowing in from the blood extraction line to be reliably discharged to an external space.

According to the present invention, the foregoing objects are attained by providing a blood reservoir comprising a main body; a blood extraction line chamber provided inside the main body and having a first connection port to which a blood extraction line is connected, the blood extraction line chamber temporarily accommodating extracted blood received via the first connection port; a suction line chamber provided inside the main body and having a second connection port to which a suction line is connected, the suction line chamber temporarily accommodating pumped-in blood received via the second connection port; a blood pooling chamber provided inside the main body and communicating with the blood extraction line chamber and the suction line chamber for pooling blood accommodated by the blood extraction line and suction line chambers, the blood pooling chamber having a blood outflow port; filtering/defoaming means arranged in a region communicating the suction line chamber and the blood pooling chamber for filtering and defoaming blood accommodated in the suction line chamber; an extracted blood inflow tube having one end communicating with the first connection port and another end open to the blood extraction line chamber, the extracted blood inflow tube being so provided as to extend at least into the blood extraction line chamber for guiding blood, which has been brought in from the blood extraction line via the first connection port, into the blood extraction line chamber; and a blood dispersing plate provided on a peripheral portion of an opening at the other end of the extracted blood inflow tube and opposing a bottom portion of the blood extraction line chamber across a predetermined distance.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

Embodiments of a blood reservoir tank according to the present invention will now be described in detail with reference to FIGS. 2 through 5.

Figure 1:
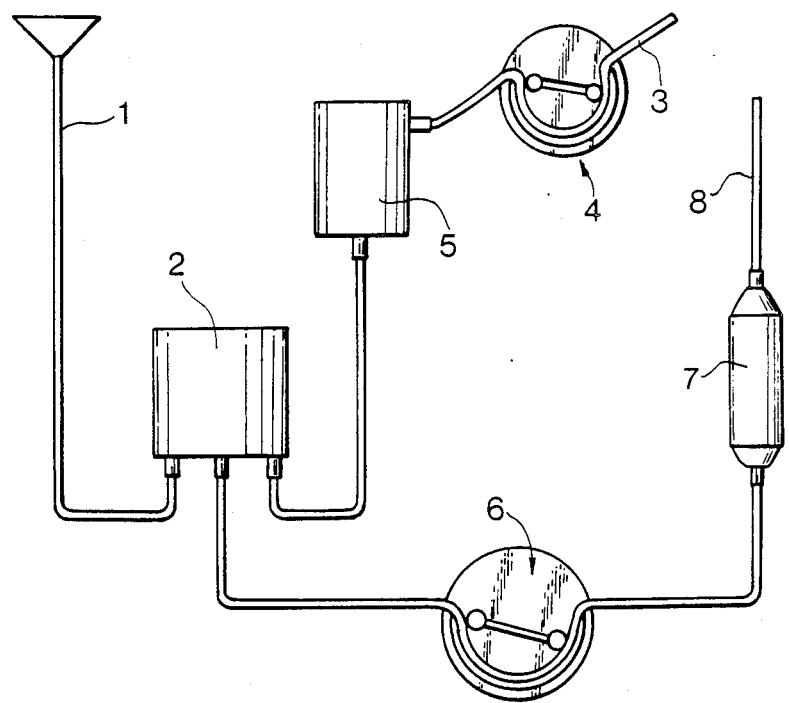
FIG. 1 is a circuit diagram schematically illustrating a conventional blood circuit having an artificial lung.
Figure 2:
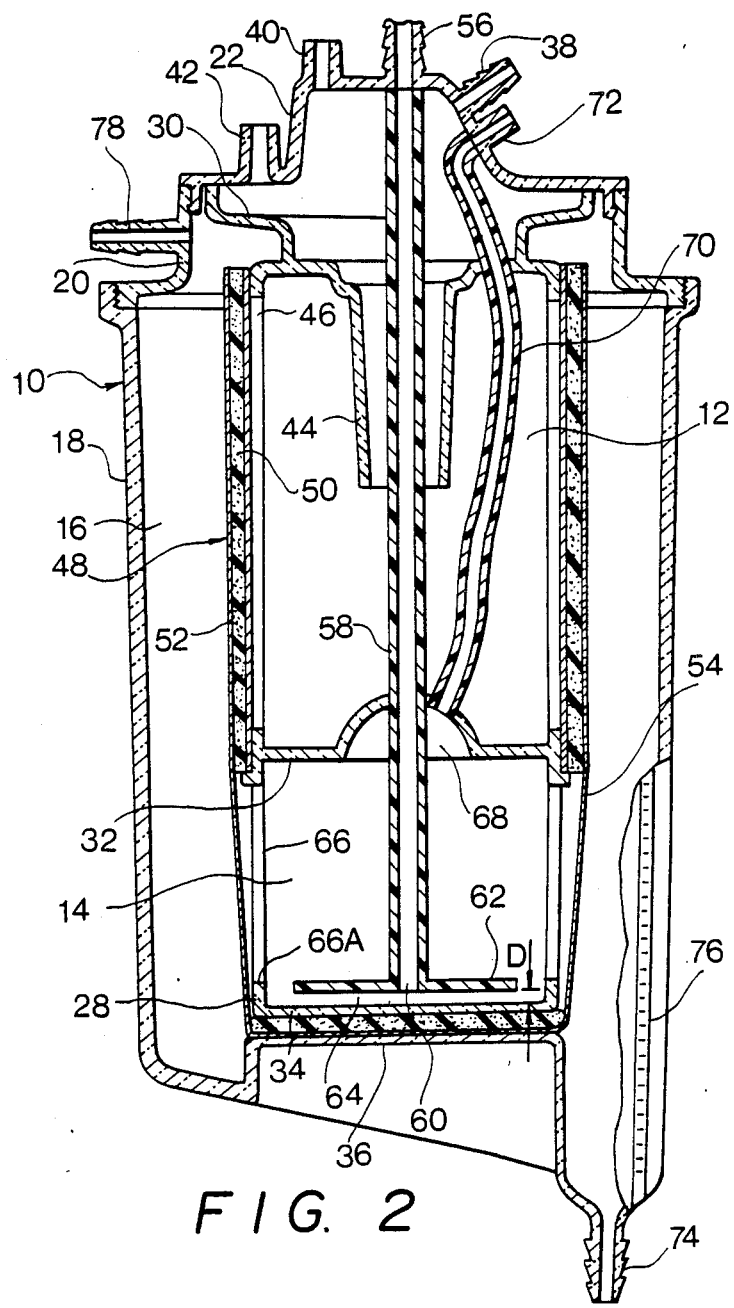
FIG. 2 is a sectional view illustrating the construction of one embodiment of a blood reservoir according to the present invention.

As shown in FIG. 2, one embodiment of a blood reservoir 10 according to the present invention includes a suction line chamber 12 which, during open-heart surgery, receives blood resulting from hemorrhage and blood filling the left ventricle or right auricle of the heart, a blood extraction line chamber 14 for receiving blood extracted from the patient's vena cava, and a pooling chamber 16 for pooling blood received by both the suction line chamber 12 and blood extraction line chamber 14.

Figure 3:
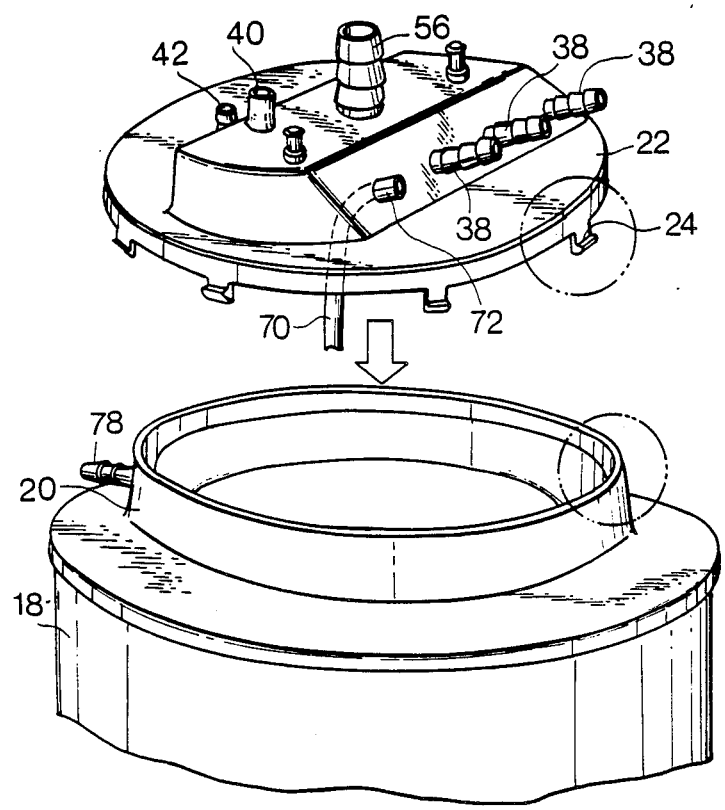
FIG. 3 is a perspective view illustrating the upper portion of the blood reservoir of FIG. 2 in detached form.
Figure 4:
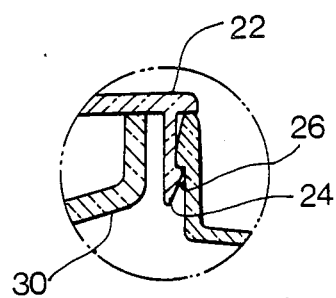
FIG. 4 is an enlarged sectional view illustrating the manner in which a cap is attached.

More specifically, the blood reservoir tank 10 comrises a cylindrically-shaped housing 18. The housing 18 has an upper end portion into which is screwed the lower end of an annularly-shaped flange 20. The flange 20 has an upper end portion to which a cap 22 is attached. As shown in FIGS. 3 and 4, the cap 22 is integrally provided on its circumferential portion with a plurality of locking tabs 24. The locking tabs 24 are lockingly engaged with an annular engagement recess 26 formed on the inner circumferential surface of the flange 20, thereby attaching the cap 22 rotatably to the flange 20.

As shown in FIG. 2, a frame-shaped member 28 is provided inside the housing 18 in generally coaxial relation therewith. The frame-shaped member 28 has an upper partitioning portion 30 in abutting contact with the lower surface of the cap 22, an intermediate partitioning portion 32 defining the bottom of the suction line chamber 12 and the ceiling of the blood extraction line chamber 14, and a lower support portion 34 forming the bottom of the blood extraction line chamber 14. The frame-shaped member 28 is held within the housing 18 with the lower support portion 34 abutting against a horizontal surface of a central upstanding portion 36 formed on the bottom portion of the housing 18 at the center thereof, and the upper partitioning portion 30 abutting against the inner circumferential surface of the cap 22. It should be noted that the upper partitioning portion 30 of the frame-shaped member 28 may be fused to the inner circumferential surface of the cap 22.

The housing 18, flange 20, cap 22 and frame-shaped member 28 are transparent and consist of a hard plastic material such as polycarbonate.

The blood pooling chamber 16 is defined between the housing 18 and frame-shaped member 28 and has a donut-shaped cross section. The suction line chamber 12 is arranged at the upper portion of the region surrounded by the blood pooling chamber 16, and the blood extraction line chamber 14 is arranged at the lower portion of this region.

More specifically, the suction line chamber 12 is defined in the blood reservoir tank 10 between the cap 22 and the intermediate partitioning portion 32 of the frame-shaped member 28. The cap 22 is provided with a suction line connection port 38, a priming connection port 40 and an air vent port 42. The upper partitioning portion 30 of the frame-shaped member 28 forms a partition between a space at the upper portion of the blood pooling chamber 16 and a space at the upper portion of the suction line chamber 12 and divides the suction line chamber 12 into upper and lower portions. Provided at the center of the upper partitioning portion 30 is a downwardly extending guide sleeve 44. The upper and lower portions of the suction line chamber 12 are communicated with each other at all times through the guide sleeve 44.

The lower portion of the suction line chamber 12 between the upper and intermediate partitioning portions 30, 32 of the frame-shaped member 28 serves as a filtering/defoaming space. Formed on the outer circumferential portion of this filtering/defoaming space is a window 46 serving as communicating means for communicating this space with the blood pooling chamber 16. The window 46 is provided with a filtering/defoaming member 48. The latter has a cylindrical filter 50 situated on the outer periphery of the window 46, and a cylindrical defoaming member 52 covering the outer surface of the filter 50. The outer surface of the defoaming member 52 is covered by a polyester tricot 54 affixed to the outer periphery of the frame-shaped member 28.

By virtue of the above construction, blood introduced from the suction line during open-heart surgery flows into the upper portion of the suction line chamber 12 from the suction line connection port 38, the blood is fed into the central portion of the filtering/defoaming space of suction line chamber 12 by the guide sleeve 44, and the blood flows out to the blood pooling chamber 16 through the filter 50 and defoaming member 52 provided in the window 46.

The filter 50 consists of a mesh of nylon or the like or an unwoven fabric and makes it possible to filter out foreign matter such as tissue and microaggregates entrained in the blood drawn in from the patient during open-heart surgery or present in a transfusion. The defoaming member 52 consists of a material such as foamed urethane coated with silicone for bubble removal and makes it possible to defoam the blood filtered by the filter 50.

The blood extraction line chamber 14 is defined in the blood reservoir chamber 10 between the intermediate partitioning portion 32 and the lower support portion 34 of the frame-shaped member 28. The central portion of the cap 22 is formed to include a blood extraction line connection port 56. Attached to the inner surface of the cap 22 is the upper end portion of an extracted blood inflow tube 58 communicating with the blood extraction line connection port 56.

In an alternative arrangement, the cap 22 can be provided at its central portion with a simple opening, and the upper end of the extracted blood inflow tube 58 can formed so as to project upwardly from this opening to serve as the blood extraction line connection port 56.

The extracted blood inflow tube 58 extends downwardly along the center of the suction line chamber 12, passes through the intermediate partitioning portion of the frame-shaped member 28 and depends into the interior of the blood extraction line chamber 14 from the partitioning portion 32. The lower end of the extracted blood inflow tube 58 has an open portion 60 the peripheral portion of which is provided with a blood dispersing plate 62 opposing, across a prescribed gap, the lower support portion 34, which is the bottom of the blood extraction line chamber 14. The surface of the lower support portion 34 on the side of the blood dispersing plate 62 is substantially planar. The same is true of the surface of the blood dispersing plate 62 on the side of the lower support portion 34. Accordingly, the lower support portion 34 and the blood dispersing plate 62 form a substantially planar space 64 between them.

The lower support portion 34 and the blood dispersing plate 62 are spaced apart from each other by a distance D, which is decided upon taking the diameter of the extracted blood inflow tube 58 in account. In other words, it is preferred that the space 64 be set in such a manner that the flow of blood exiting downwardly from the extracted blood inflow tube 58 not be impeded, namely that the downward blood flow not be met with resistance. More specifically, the distance D between the lower support portion 34 and the blood dispersing plate 62 preferably is 1/5-⅔, especially ¼-½, the diameter of the extraction blood inflow tube 58.

The portion of the frame-shaped member 28 located between the intermediate partitioning plate 32 and the lower support portion 34 is formed to include in its circumferential wall a window 66 serving as means for communicating the blood extraction line chamber 14 and the blood pooling chamber 16. The window 66 has a lower edge 66A which is designed to be on substantially the same level as the blood dispersing plate 62. The outer surface of the window 66 is covered by the polyester tricot 54 affixed to the outer periphery of the frame-shaped member 28.

The lower surface of the intermediate partitioning portion 32 of frame-shaped member 28, namely the ceiling portion of the blood extraction line chamber 14, is formed to include a hemispherical or dome-shaped air capture section 68 projecting upwardly from the top of the chamber 14. Alternatively, the air capture section 68 can have the configuration of a circular cone rather than a hemisphere. Connected to the uppermost part of the air capture section 68 is the lower end of an air discharge tube 70, which also functions as a connection port for a medical fluid injection line. The upper end of the air discharge tube 70 is connected to the air vent port 72 formed in the cap 22. Note that the extracted blood inflow tube 58 penetrates the central portion of the air capture section 68.

With the above-described arrangement, venous blood introduced from the blood extraction line flows into the extracted blood inflow tube 58 from the blood extraction line connection port 56, through the outflow space 64 defined between the blood dispersing plate 62 and the bottom of the blood extraction line chamber 14, into the chamber 14 and thence from the chamber 14 out to the blood pooling chamber 16 via the window 66.

A blood outflow port 74 is formed in the lowermost end of the housing 18 at the part defining the blood pooling chamber 16. Here the bottom of the blood pooling chamber 16 forms an inclined surface which places the blood outflow port 74 at the lowermost level of the tank, whereby all of the blood within the blood pooling chamber 16 is capable of flowing out of the blood outflow port 74. The latter has a funnel-shaped configuration. Thus, blood which exits from the outflow port 74 forms a vortex flow along the funnel-shaped wall surface of the port. This makes it possible to prevent bubbles from forming and mixing in with the outflowing blood.

The surface of the housing 18 is provided with graduations 76 indicating the level of pooled blood. Further, the flange 29 is formed to include an air vent port 78 communicating with the space at the top of the blood pooling chamber 16.

Let us now describe the operation of the blood reservoir 10 of the above-described embodiment of the invention.

Figure 5:
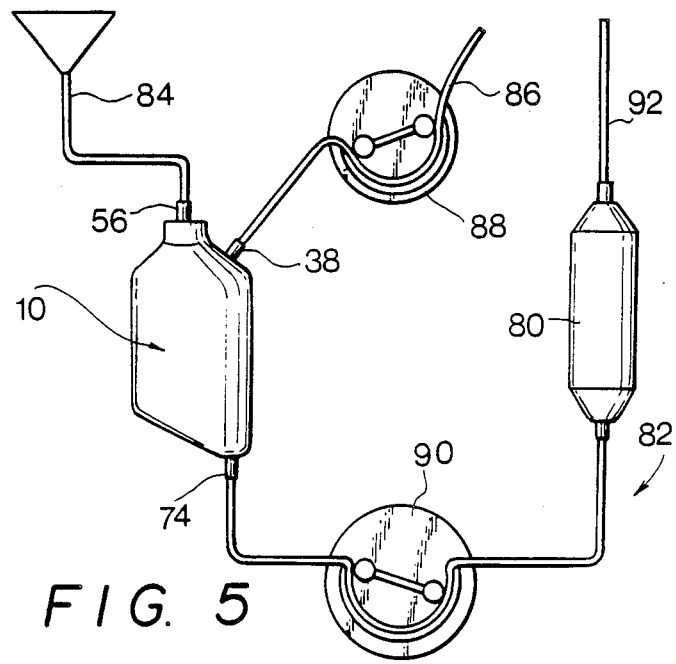
FIG. 5 is a circuit diagram schematically illustrating a blood circuit using the blood reservoir shown in FIG. 2.

Described first with reference to FIG. 5 will be a blood circuit 82 having the blood resevor 10 and an artifical lung 80 equipped with a heat exchanger. As shown in FIG. 5, blood extracted from the patient's vena cava enters the blood extraction line chamber 14 from the blood extraction line connection port 56, which receives the blood from a blood extraction line 84. The blood then enters the blood pooling chamber 16 via the window 66. During open-heart surgery, blood resulting from hemorrhage and blood filling the left ventricle or right auricle of the heart is drawn in via a suction line 86 and first pump 88, enters the suction line chamber 12 from the suction line connection port 38 and then flows into the blood pooling chamber 16 via the filtering/defoaming member 48. Blood which temporarily collects in the blood pooling chamber 16 of the blood reservoir 10 is delivered to the artificial lung 80 by a second pump 90. The blood delivered to the artificial lung 80 is adjusted in temperature and oxygenated therein before being returned to the patient's body via a blood delivery line 92. In moving from the suction line chamber 12 to the blood pooling chamber 16 within the blood reservoir 10, the blood is filtered of foreign matter by the filter 50 and is defoamed by the defoaming member 52.

Thus, with the blood reservoir 10 described above, the suction line chamber 12, which functions as the conventional cardiotomy reservoir and communicates with the suction line 86, is provided in addition to the blood extraction line chamber 14 communicating with the blood extraction line 84. Also provided is the blood pooling chamber 16, which is in direct communication with the suction line chamber 12 and blood extraction line chamber 14. Accordingly, the blood reservoir 10 reduces the amount of blood which flows extracorporeally during open-heart surgery, makes it simpler to assemble the circuit of the artificial lung and simplifies the monitoring of the blood pooling level.

Further, in the blood reservoir 10, the blood dispersing plate 62 is provided on the periphery of the opening at the end of the extracted blood inflow tube, which opens into the blood extraction line chamber 14. Accordingly, the entrant blood from the blood extraction line 84 is capable of being gently dispersed in the blood extraction line chamber 14 in a regulated state and, hence, the blood is capable of flowing into the chamber 14 in a state free of microbubbles.

Further, in the blood reservoir 10 of the invention, the ceiling portion of the blood extraction line chamber 14 is provided with the air capture section 68. Accordingly, air which floats upwardly in the blood inside the blood extraction line chamber 14 can be captured in positive fashion by the air capture section 68. This makes it possible for the air contained in bubbles separated from the entrant blood received from the blood extraction line 84 to be discharged to the outside in a positive manner without being carried into the blood pooling chamber 16.

Furthermore, in the blood reservoir 10, the suction line chamber 12 is arranged in the upper part of the region surrounded by the donut-shaped blood pooling chamber 16, and the blood extraction line chamber 14 is arranged at the lower part of this region. As a result, the blood level prevailing inside the blood reservoir tank 10 when the blood flows into the tank can be set to be higher than the blood dispersing plate 62 at all times. Accordingly, the blood which flows out of the space 64 between the blood dispersing plate 62 and the lower support portion 34 flows into blood that has already collected. When the blood flows from the blood extraction line chamber 14 to the blood pooling chamber 16, therefore, the blood can be prevented from forming air bubbles.

In the blood reservoir 10, the suction line connection port 38 to which the suction line 86 is connected, the blood extraction line connection port 56 to which the blood extraction line 84 is connected, the priming connection port 40 to which a priming line is connected, and the air discharge tube 70 to which a medical fluid injection line can be connected, are all formed in the cap 22, and the cap 22 is capable of being rotated relative to the flange 20 and housing 18. Accordingly, rotating the cap 22 allows the various connection ports to be freely aligned with the various lines to facilitate piping.

Further, the blood reservoir 10 is provided with the cylindrical guide sleeve 44 for guiding the blood that has flowed into the upper portion of the suction line chamber 12 into the central portion of the underlying filtering/defoaming space. Accordingly, the blood in the upper portion flows between the extracted blood inflow tube 58 and the guide sleeve 44, with the blood flowing along the outer wall of the tube 58 below the tip of the guide sleeve 44. This is desirable since air bubbles will not be produced in the blood.

Figure 6:
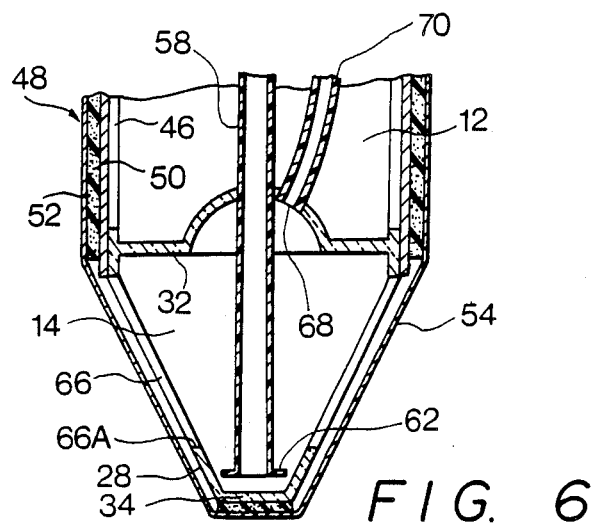
FIG. 6 is a sectional view showing the details of a principal portion of another embodiment of a blood reservoir according to the present invention.

In the above embodiment, the blood dispersing plate 62 provided on the opening of the extracted blood inflow tube 58 is described as being set at approximately the same level as the lower edge 66A of the window 66. However, the invention is not limited to such an arrangement. In FIG. 6, which illustrates another embodiment of the invention, the level of the blood dispersing plate, shown at number 62, is set to be lower than that of the lower edge 66A of window 66.

A blood reservoir in accordance with the invention was fabricated and subjected to an experiment, the results of which will now be described.

The housing 18, having a volume of about 2300 cm$^3$, was provided with the suction line chamber 12 (volume: 500 cm$^3$) having the filter 50, the filtering area of which was 280 cm$^2$, and with the blood extraction line chamber 14 (volume: 300 cm$^3$). Cow blood was circulated through the tank to test its filtering and microbubble prevention functions. The cow blood used had a temperature of 25°–30° C. and contained fresh heparin having an Ht value of 32%. The cow blood was circulated for one hour at a flow rate of 500 cm$^3$/min in the suction line 86 and 6000 cm$^3$/min in the blood extraction line 84. Air bubbles were occasionally mixed with the blood in the blood extraction line 84 to check the degree of microbubble formation. As for the filtering function using glass beads, the results of the experiment showed that 90% of 40 μm foreign matter and 70% of 20 μm foreign matter were eliminated. As for the microbubble prevention function, absolutely no outflow of microbubbles to the blood pooling chamber 16 was found even when air was injected from the inlet to the blood extraction line 84 intermittently in amounts of about 50 cm$^3$. In the prototype fabricated, the diameter of the extracted blood inflow tube 58 was 100 mm, and the distance D between the lower support portion 34 and the blood diffusing plate 62 was 3 mm.

What is claimed is:

1. A blood reservoir comprising:
   a main body;
   a blood extraction line chamber provided inside said main body and having a first connection port to which a blood extraction line is connected, said blood extraction line chamber temporarily accommodating blood extracted from a blood vessel and received via the first connection port;
   a suction line chamber provided inside said main body and having a second connection port to which a suction line is connected, said suction line chamber temporarily accommodating pumped-in blood requiring filtering/defoaming and received via the second connection port;
   a blood pooling chamber provided inside said main body and communicating with said blood extraction line chamber and said suction line chamber for pooling blood accommodated by said blood extraction line and suction line chambers, said blood pooling chamber having a blood outflow port;
   filtering/defoaming means arranged in a region communicating said suction line chamber and said blood pooling chamber for filtering and defoaming blood accommodated in said suction line chamber;
   an extracted blood inflow tube having one end communicating with the first connection port and another end open to said blood extraction line chamber, said extracted blood inflow tube being so provided as to extend at least into said blood extraction line chamber for guiding blood, which has been brought in from the blood extraction line via the first connection port, into said blood extraction line chamber; and
   a blood dispersing plate attached to and extending laterally from a peripheral portion of an opening at said another end of said extracted blood inflow tube and opposing a bottom portion of said blood extraction line chamber across a predetermined distance.

2. The blood reservoir according to claim 1, wherein said main body comprises a cylindrical housing and a frame-shaped member provided inside the housing, said frame-shaped member having an outer circumference spaced away from an inner circumference of the housing and an intermediate partitioning portion separating an internal space of said frame-shaped member into upper and lower portions;
   said blood pooling chamber is defined between the housing and the frame-shaped member;
   said suction line chamber is defined in a portion above the intermediate partitioning portion in a space surrounded by the frame-shaped member; and
   said blood extraction line chamber is defined in a portion below the intermediate partitioning portion in a space surrounded by the frame-shaped member.

3. The blood reservoir according to claim 2, wherein said frame-shaped member has a first window portion above the intermediate partitioning portion for communicating said suction line chamber and said blood pooling chamber, and a second window portion below the intermediate partitioning portion for communicating said blood extraction line chamber and said blood pooling chamber.

4. The blood reservoir according to claim 3, wherein said filtering/defoaming means is provided on the periphery of said first window portion.

5. The blood reservoir according to claim 4, wherein said filtering/defoaming means has a filter for filtering blood in said suction line chamber, and a defoaming member provided on an outer circumference of said filter for eliminating bubbles from the blood.

6. The blood reservoir according to claim 2, wherein a bottom portion of said housing is provided at an incline, and said blood outflow port is provided at a lowermost end of the bottom portion of said housing.

7. The blood reservoir according to claim 2, wherein a bottom portion of said housing defines the bottom portion of said blood extraction line chamber and has a planar configuration, and a lower surface of said blood dispersing plate opposing a bottom portion of the frame-shape member has a planar configuration.

8. The blood reservoir according to claim 7, wherein the bottom portion of said frame-shaped member lies parallel to the blood dispersing plate.

9. The blood reservoir according to claim 1, further comprising:
   air capture means having an upwardly extending cavity at a ceiling portion of said blood extraction line chamber for capturing air brought into said blood extraction line chamber, and
   discharge means provided between the air capture means and the main body for discharging air captured by said air capture means to the outside of the main body.

10. The blood reservoir according to claim 9, wherein said main body comprises a cylindrical housing and a frame-shaped member provided inside the housing, said frame-shaped member having an outer circumference spaced away from an inner circumference of the housing and an intermediate partitioning portion separating an internal space of said frame-shaped member into upper and lower portions;
   said blood pooling chamber is defined between the housing and the frame-shaped member;
   said suction line chamber is defined in a portion above the intermediate partitioning portion in a space surrounded by the frame-shaped member; and
   said blood extraction line chamber is defined in a portion below the intermediate partitioning portion in a space surrounded by the frame-shaped member.

11. The blood reservoir according to claim 10, wherein said intermediate partitioning portion has an upwardly extending projection, a space internally of said projection defining the upwardly projecting cavity of the air capture means.

12. The blood reservoir according to claim 11, wherein said upwardly extending cavity is hemispherical.

13. The blood reservoir according to claim 2, wherein said main body has a cap portion rotatably provided on an upper portion of the housing.

14. The blood reservoir according to claim 13, wherein said first and second connection ports are formed in said cap portion.

15. The blood reservoir according to claim 14, wherein said cap portion has a priming connection port and an air vent port.

16. The blood reservoir according to claim 2, further comprising a tricot so provided as to cover said frame-shaped member.

* * * * *